(12) United States Patent
Suther et al.

(10) Patent No.: US 11,380,429 B1
(45) Date of Patent: Jul. 5, 2022

(54) ELASTIC DATA PRIVACY-COMPLIANT HEALTHCARE ANALYTICS

(71) Applicant: Change Healthcare Holdings, LLC, Nashville, TN (US)

(72) Inventors: Tim Suther, Nashville, TN (US); Anil Konda, Nashville, TN (US); Jaideep Kulkarni, Nashville, TN (US); Robert Stagno, Nashville, TN (US); Ravichandra Bangaru, Nashville, TN (US)

(73) Assignee: Change Healthcare Holdings, LLC, Nashville, TN (US)

( * ) Notice: Subject to any disclaimer, the term of this patent is extended or adjusted under 35 U.S.C. 154(b) by 246 days.

(21) Appl. No.: 16/884,429

(22) Filed: May 27, 2020

(51) Int. Cl.
| | |
|---|---|
| *G16H 10/60* | (2018.01) |
| *G06F 8/61* | (2018.01) |
| *G06F 21/56* | (2013.01) |
| *G06F 21/57* | (2013.01) |
| *G06F 21/62* | (2013.01) |
| *G06Q 50/26* | (2012.01) |
| *G16H 50/20* | (2018.01) |
| *H04L 9/40* | (2022.01) |

(52) U.S. Cl.
CPC ............... *G16H 10/60* (2018.01); *G06F 8/61* (2013.01); *G06F 21/562* (2013.01); *G06F 21/57* (2013.01); *G06F 21/6254* (2013.01); *G06Q 50/265* (2013.01); *G16H 50/20* (2018.01); *H04L 63/0209* (2013.01); *H04L 63/0428* (2013.01); *G06F 2221/032* (2013.01); *G06F 2221/033* (2013.01); *G06Q 2220/10* (2013.01)

(58) Field of Classification Search
CPC .......... G16H 10/60; G16H 50/20; G06F 8/61; G06F 21/562; G06F 21/57; G06F 21/6254; G06F 2221/032; G06F 2221/033; G06Q 50/265; G06Q 2220/10; H04L 63/0209; H04L 63/0428
See application file for complete search history.

(56) References Cited

U.S. PATENT DOCUMENTS

| | | | |
|---|---|---|---|
| 8,316,054 B2 * | 11/2012 | El Emam | G06F 16/284 |
| | | | 713/189 |
| 10,380,381 B2 * | 8/2019 | Scaiano | G06F 21/6254 |
| 10,635,837 B1 * | 4/2020 | Jun | G16H 10/60 |
| 10,706,447 B2 * | 7/2020 | Barday | G06Q 50/265 |
| 10,708,305 B2 * | 7/2020 | Barday | H04L 63/126 |
| 11,004,548 B1 * | 5/2021 | Austin | H04L 9/3226 |
| 11,042,668 B1 * | 6/2021 | Kassam-Adams | G06F 21/572 |
| 11,120,144 B1 * | 9/2021 | Kassam-Adams | |
| | | | G06F 21/6245 |
| 2015/0007249 A1 * | 1/2015 | Bezzi | G06F 21/6227 |
| | | | 726/1 |
| 2015/0213202 A1 * | 7/2015 | Amarasingham | G16H 50/50 |
| | | | 705/2 |
| 2015/0339496 A1 * | 11/2015 | El Emam | G06F 21/6227 |
| | | | 726/26 |
| 2016/0127367 A1 * | 5/2016 | Jevans | H04W 12/10 |
| | | | 713/152 |
| 2017/0083719 A1 * | 3/2017 | Scaiano | G06F 21/6254 |

(Continued)

*Primary Examiner* — Darren B Schwartz
(74) *Attorney, Agent, or Firm* — Meunier Carlin & Curfman LLC

(57) ABSTRACT

Disclosed and described herein are systems, methods and computer program products providing elastic data privacy-compliant healthcare analytics that enables privacy certification on a case-by-case basis.

20 Claims, 3 Drawing Sheets

(56) References Cited

U.S. PATENT DOCUMENTS

| | | | |
|---|---|---|---|
| 2017/0161521 A1* | 6/2017 | Fontecchio | H04L 9/14 |
| 2017/0177907 A1* | 6/2017 | Scaiano | G06N 7/005 |
| 2018/0262519 A1* | 9/2018 | Arunkumar | G06F 16/258 |
| 2019/0013950 A1* | 1/2019 | Becker | H04L 9/3247 |
| 2019/0266353 A1* | 8/2019 | Gkoulalas-Divanis | G06F 21/602 |
| 2019/0272387 A1* | 9/2019 | Gkoulalas-Divanis | G06F 21/604 |
| 2020/0167484 A1* | 5/2020 | Linton | G06F 8/41 |
| 2020/0394320 A1* | 12/2020 | Bernau | G06F 21/6254 |
| 2021/0165913 A1* | 6/2021 | Besanson | G06F 21/6227 |
| 2021/0192078 A1* | 6/2021 | Cosman | G06N 20/00 |
| 2021/0279355 A1* | 9/2021 | Otte | G06F 21/6218 |
| 2021/0279367 A1* | 9/2021 | Khan | G06F 16/221 |
| 2021/0334403 A1* | 10/2021 | Luus | G06F 21/6245 |

* cited by examiner

```
┌─────────────────────────────────────────────────────────────────────┐
│ Receive in a secure hosted environment customer data comprised at   │
│ least in part of PHI corresponding to one or more individuals       │
│                              202                                    │
└─────────────────────────────────────────────────────────────────────┘
                                  │
┌─────────────────────────────────────────────────────────────────────┐
│ Create encrypted tokens for the PHI corresponding to one or more    │
│ individuals                                                         │
│                              204                                    │
└─────────────────────────────────────────────────────────────────────┘
                                  │
┌─────────────────────────────────────────────────────────────────────┐
│ Receive in the secure hosted environment deidentified customer data │
│ that includes one or more required customer attributes              │
│                              206                                    │
└─────────────────────────────────────────────────────────────────────┘
                                  │
┌─────────────────────────────────────────────────────────────────────┐
│ Receive in the secure hosted environment health data encrypted      │
│ tokens created for aggregated deidentified health data from a       │
│ deidentified healthcare information dataset  208                    │
└─────────────────────────────────────────────────────────────────────┘
                                  │
┌─────────────────────────────────────────────────────────────────────┐
│ Receive in the secure hosted environment a pre-built executable     │
│ software package that is installed in a secure container in the     │
│ secure hosted environment, wherein the pre-built executable         │
│ software package comprises computer-executable code to learn and    │
│ train one or more models using the encrypted tokens and the health  │
│ data encrypted tokens, and wherein the pre-built executable         │
│ software package includes business rules to ensure that training of │
│ the one or more models does not increase a risk of re-identification│
│ of the PII corresponding to the one or more individuals  210        │
└─────────────────────────────────────────────────────────────────────┘
                                  │
┌─────────────────────────────────────────────────────────────────────┐
│ Review outputs from the one or more models by a data privacy review │
│ and certifying the outputs to ensure the risk of re-identification  │
│ of the PHI corresponding to the one or more individuals remains at  │
│ or below one or more thresholds of the risk of re-identification of │
│ the PII corresponding to the one or more individuals 212            │
└─────────────────────────────────────────────────────────────────────┘
                                  │
┌─────────────────────────────────────────────────────────────────────┐
│ Deliver from the secure hosted environment, a binary of a model,    │
│ statistical scoring model, or an aggregate report from the one or   │
│ more models if the risk of re-identification of the PHI             │
│ corresponding to the one or more individuals remains at or below    │
│ the one or more thresholds as determined and certified by the data  │
│ privacy review 214                                                  │
└─────────────────────────────────────────────────────────────────────┘
```

FIG. 2

ELASTIC DATA PRIVACY-COMPLIANT HEALTHCARE ANALYTICS

BACKGROUND

When combining de-identified data with external demographic data or when applying de-identified data to small populations, there is heightened risk of re-identification. Accordingly, compliance officers significantly and rightfully restrict the use of de-identified data to protect against such re-identification. While effectively protecting privacy, much predictive power is foregone, negatively impacting organizational effectiveness and efficiency. In healthcare specifically, many organizations rely on the expert method to certify data privacy compliance (e.g., HIPAA compliance), which certifies all possible uses and data combinations at once. Under this conventional method, a single outlier use restricts the availability of data for all uses. Ironically then, the greater the number of potential uses, the more restricted usage will be. In healthcare, outcomes and cost-effectiveness are negatively affected.

The conventional legacy approach is referred to as inelastic analytics, because the data privacy certification process is one size fits all, lacking the elasticity to adjust to the risk of the actual use. Inelastic analytics particularly restricts the use of advanced analytics in audience activation, advanced measurement and attribution, small populations (rare diseases, specialty drugs), risk/contract modeling, member engagement, especially new members, willingness to treat, ability to pay, and likelihood to comply. Together, these represent powerful steps that can improve healthcare outcomes and economics.

Under conventional inelastic healthcare analytics, the expert opinion method certifies data privacy (e.g., HIPAA) compliance by statistically analyzing all possible use cases of the data and data combinations at once. Given all possible uses are assessed at once, the highest risk use and or data combination determines the type and number of attributes allowed. In other words, a single outlier restricts availability of data for all uses, no matter the actual risk of use. This significantly impairs healthcare constituents seeking to predict healthcare outcomes.

Thus, there is a desire to responsibly use more data for predictions, while remaining rigorously compliant with privacy regulations that in a way that overcomes challenges in the art, some of which are described herein. More specifically, there is a need to allow the combination of demographic data and any/all consumer attributes with appropriately de-identified health data in such a way that it is possible to execute use cases while adhering to all privacy regulations and guidelines.

BRIEF SUMMARY

Generally, disclosed and described herein are methods, systems and computer program products for providing elastic data privacy-compliant healthcare analytics that enables privacy certification on a case-by-case basis.

Generally, a secure hosted environment is provided wherein data licensees upload datasets, combine the datasets with de-identified healthcare data, iteratively develop/train models using methodologies of their choosing, receive privacy certification for specific uses, and output results (including binary scoring algorithms, statistical scoring model, or an aggregate report), all without ever receiving de-identified healthcare data. This allows the data licensee to create and access an integrated dataset, comprised of de-identified healthcare information and their own, to develop/train a model that the data licensee can then take and use going forward. Data privacy certification is done on a case-by-case basis, dramatically increasing data available for modeling for most uses. Unlike with inelastic analytics where the number of de-identified individual attributes is severely restricted (typically less than five), embodiments described herein make thousands of attributes available.

With conventional inelastic analytics, use of real-world health data with small populations like rare disease and specialty drugs are highly restricted and likely not usable. With the embodiments described herein, these uses are achievable and compliant.

With conventional inelastic analytics, advanced modeling and analytics are not achievable at scale (examples: advanced audience selection, advanced measurement and attribution, risk assessment and contract modeling, willingness to treat, ability to pay, and likelihood to comply). With the embodiments described herein, all these use cases are achievable at scale.

A general description of the process described herein, which is all automated, comprises a customer (e.g., data licensee) first providing a use case (i.e., want to predict X) and an independent dataset that can be scored; the information is delivered to a secure hosted environment, where a data repository of de-identified healthcare information can be accessed, which can be combined with the customer's independent dataset to train/score a model that meets their use case. Once developed and trained, the customer's model is checked to determine whether the trained model complies with data privacy laws and regulations (e.g., HIPAA). If the model passes, the customer is provided a binary scoring algorithm—math that can be applied against an independent dataset (e.g., these three attributes in data have this relative importance, so combine based on this formula and with these specific weights), or the customer is provided with a statistical scoring model for their dataset using the developed binary scoring algorithm, or an aggregate report.

In one aspect, methods of providing data privacy-compliant healthcare analytics are described. One embodiment of the method comprises receiving, in a secure hosted environment, customer data, wherein at least a portion of the customer data comprises personally identifiable information (PII) and/or protected health information (PHI) (hereinafter referred to collectively as "PHI") corresponding to one or more individuals. Encrypted tokens are created for the PHI corresponding to the one or more individuals. De-identified customer data is received in the secure hosted environment, wherein the de-identified customer data includes one or more required consumer attributes. Health data encrypted tokens are created for aggregated de-identified health data from a de-identified healthcare information dataset. The health data encrypted tokens for the aggregated de-identified health data are received in the secure hosted environment. Further received in the secure hosted environment is a pre-built executable software package that is installed in a secure container in the secure hosted environment. The pre-built executable software package comprises computer-executable code to learn and train one or more models using the encrypted tokens and the health data encrypted tokens. The pre-built executable software package includes business rules to ensure that training of the one or more models does not increase a risk of re-identification of the PHI corresponding to the one or more individuals. In some instances, the secure container in the secure hosted environment may comprise a Docker container in Amazon Web Services (AWS). Outputs from the one or more models are reviewed during a data privacy review and the outputs are certified to ensure the risk of re-identification of the PHI corresponding to the one or more individuals remains at or below one or more thresholds of the risk of re-identification of the PHI corresponding to the one or more individuals. A binary of a model, statistical scoring model, or an aggregate report from the one or more models are delivered from the secured hosted environment to a data licensee if the risk of re-identification of the PHI corresponding to the one or more individuals remains at or below the one or more thresholds as determined and certified by the data privacy review.

In some instances, the secure hosted environment comprises a cloud infrastructure behind a firewall or protected in some other manner.

In various instances, the customer data and/or the de-identified customer data is delivered to the secure hosted environment using any secure communications method. For example, the secure communication method may comprise one of sftp, s3 transfer, and the like.

In some instances, the health data encrypted tokens are created using the same tokenization process used to create the encrypted tokens for the PHI corresponding to the one or more individuals.

In some instances, the pre-built executable software may be scanned for any malicious code prior to its installation in the secure container.

In some instances, all thresholds of the risk of re-identification of the PHI corresponding to the one or more individuals, whether met or unmet, are logged within the secure hosted environment for audit purposes.

In some instances, the binary of a model, statistical scoring model, or an aggregate report from the one or more models are delivered to the data licensee if the risk of re-identification of the PHI corresponding to the one or more individuals remains at or below the one or more thresholds as determined and certified by the data privacy review. In some instances, an application programming interface (API) may be installed at an edge of the secure hosted environment, with all necessary controls, that allows the data licensee access to only access the API, wherein any inputs to the API are pre-defined and certified by the data privacy review.

Generally, the customer data comprises a use case provided by the data licensee. For example, the use case may comprise one or more of audience development, program measurement, multi-channel attribution, campaign optimization, "same store" analysis, identify and act on emerging trends, machine Learning and artificial intelligence (AI) algorithms, HCP practice behavior/brand loyalty, planning and strategy, analytics and predictive modeling, referral leakage, benchmarking and competitive analysis, and the like.

In some instances, the data privacy review comprises a review for HIPAA compliance.

In some instances, one of the business rules ensuring that training of the one or more models does not increase the risk of re-identification of the PHI corresponding to the one or more individuals comprises the business rule ensuring that training of the one or more models does not happen on very small cohorts.

Generally, the aggregated de-identified health data from a de-identified healthcare information dataset is obtained from one or more of medical claims, medical remittances, pharmacy claims, dental claims, dental remittances, lab orders, lab results, and the like.

In some instances, the one or more required consumer attributes comprise more than five required consumer attributes. For example, the one or more required consumer attributes may be 1000 or more.

Further disclosed and described herein are systems and computer-program products for implementing the above-described methods.

Other objects and advantages will become apparent to the reader and it is intended that these objects and advantages are within the scope of the present invention. To the accomplishment of the above and related objects, this invention may be embodied in the form illustrated in the accompanying drawings, attention being called to the fact, however, that the drawings are illustrative only, and that changes may be made in the specific construction illustrated and described within the scope of this application.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein:

FIG. 2 is a flowchart illustrating an example of a process for performing elastic providing data privacy-compliant healthcare analytics.

DETAILED DESCRIPTION

Figure 1:
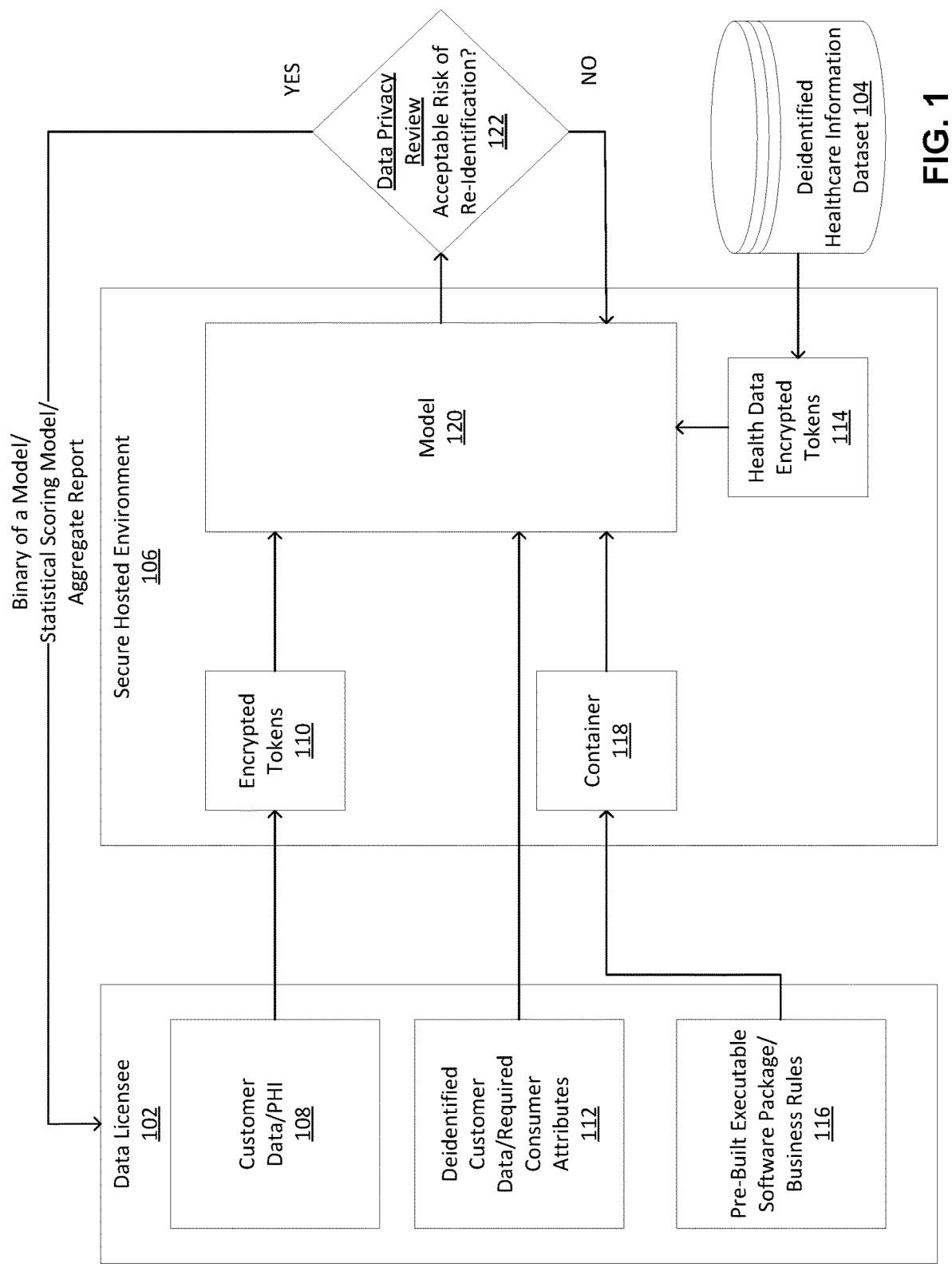
FIG. 1 illustrates an exemplary overview block diagram for performing aspects of the disclosed embodiments.

Before the present methods and systems are disclosed and described, it is to be understood that the methods and systems are not limited to specific synthetic methods, specific components, or to particular compositions. It is also to be understood that the terminology used in this entire application is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, to "about" another particular value, or from "about" one value to "about" another value. When such a range is expressed, another embodiment includes from the one particular value, to the other particular value, or from the one particular value to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

As will be appreciated by one skilled in the art, the methods and systems may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium may be utilized including hard disks, CD-ROMs, DVD-ROMs, optical storage devices, or magnetic storage devices.

Embodiments of the methods and systems are described below with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These computer program instructions may be loaded onto a general-purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

Additionally, the disclosed system, method and computer-program product can optionally be implemented within a cloud computing environment, for example, in order to decrease the time needed to perform the algorithms, which can facilitate processing of a health claim as software-as-a-service (SaaS). Cloud computing is well-known in the art. Cloud computing enables network access to a shared pool of configurable computing resources (e.g., networks, servers, storage, applications, and services) that can be provisioned and released with minimal interaction. It promotes high availability, on-demand self-services, broad network access, resource pooling and rapid elasticity. It should be appreciated that the logical operations described herein with respect to the various figures may be implemented (1) as a sequence of computer implemented acts or program modules (i.e., software) running on a computing device, (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

The present methods and systems may be understood more readily by reference to the following detailed description of preferred embodiments and the Examples included therein and to the Figures and their previous and following description.

A. Overview

Described herein are embodiments of a system, method and computer program product (including SaaS) where customers create unique model training datasets comprised of data provided by customers (for example, demographic data, ad log impressions, population cohorts) which are tokenized and linked to a de-identified repository of healthcare information.

With these unique training datasets, customers perform iterative model training and development. In contrast to certifying all possible uses and data combinations at once, each model is individually certified only when based on a minimum training set size and when producing a minimum number of true positives or true negatives as determined by a data privacy review.

If certified, the utility returns a binary scoring algorithm or statistical scoring model, which cannot use any de-identified healthcare data or individual tokens or record identifiers to score, nor can be used to re-identify individuals. Furthermore, no de-identified healthcare data is provided to customer. In other aspects, the customer may be provided an aggregate report. Multiple statistical methodologies are available for the model, including regression, classification and machine learning.

All model training and development is performed in a secure hosted environment, and activity is logged for auditing/compliance purposes.

Healthcare information, such as information obtained from one or more of medical claims, medical remittances, pharmacy claims, dental claims, dental remittances, lab orders, lab results, and the like can be collected and de-identified in order to create a de-identified healthcare information dataset. Generally, the healthcare information is de-identified using the expert determination method under HIPAA regulations, though other methods may be used. This information dataset is useful in that analytics can be performed for various use cases including, for example, audience development, program measurement, multi-channel attribution, campaign optimization, "same store" analysis, identify and act on emerging trends, machine learning and artificial intelligence (AI) algorithms, HCP practice behavior/brand loyalty, planning and strategy, analytics and predictive modeling, referral leakage, benchmarking and competitive analysis, and the like. However, when the use cases focus on healthcare information with a small set of cohorts (e.g., number of persons with a very rare disease), or the use case utilizes a large number of attributes of the healthcare information, there is a risk of re-identification of the healthcare information in violation of data privacy laws and regulations such as HIPAA (Health Insurance Portability and Accountability Act). Attributes of the healthcare information may include, for example, disease states, procedures, prescriptions, lab orders/results, durable medical equipment (DME), medical supplies, care setting, reimbursement model, entities, transaction counts, transaction cycle time, billed and adjudicated amounts, unique patient counts, co-morbidities, rejects/reversals, new/switchers, adherence, outcomes/readmits, geographical data, demographic data, segments data (e.g., provider, payer, employer group, etc.), frequency of data collection, and the like.

Because of the risk of possible re-identification, conventional inelastic analytics takes a very conservative approach ("worst case") when providing results of a use case, which limits use of the de-identified healthcare information dataset. The embodiments described herein overcome that challenge by evaluating each use case on a case-by-case basis and providing data privacy certification when the risk of re-identification from the use case is at or below a determined threshold.

FIG. 1 illustrates an example overview block diagram for performing aspects of the disclosed embodiments including providing data privacy-compliant healthcare analytics. In FIG. 1, a data licensee 102 (a person or entity who wants to analyze a de-identified healthcare information dataset 104) using a use case provides, to a secure hosted environment 106, customer data 108, wherein at least a portion of the customer data 108 comprises PHI corresponding to one or more individuals. Examples of use cases include audience development, program measurement, multi-channel attribution, campaign optimization, "same store" analysis, identify and act on emerging trends, machine learning and artificial intelligence (AI) algorithms, HCP practice behavior/brand loyalty, planning and strategy, analytics and predictive modeling, referral leakage, benchmarking and competitive analysis, and the like. Where audience development generally refers to a process of determining who might be receptive to advertising (though de-identified data may never be used directly for these purposes); program measurement, multichannel attribution & campaign optimization are generally measures of whether marketing and/or advertising initiatives actually caused changes in real world behavior; same store analysis is an analysis that compares year over year changes in profile/outcomes; identify and act on emerging trends is the identification of "out of threshold" behavior that represents something new, something out of the ordinary; HCP practice behavior/brand loyalty comprises understanding the prescribing behavior of healthcare providers, and/or patients preferences for HCPs; planning and strategy generally refers to a broad assessment in healthcare activity that identifies critical changes that senior executives must be aware of, and act upon; and referral leakage generally comprises analysis of changes in the relationships between PCPs and health systems.

In some instances, the secure hosted environment 106 comprises a cloud infrastructure. Generally, the cloud infrastructure exists behind a firewall or is protected by other security mechanisms. Once received in the secure hosted environment 106, encrypted tokens 110 are automatically created for the PHI corresponding to the one or more individuals. The data licensee 102 further provides to the secure hosted environment 106 de-identified customer data 112, wherein the de-identified customer data 112 includes one or more required consumer attributes. Consumer attributes may generally include, for example, geodemographic information, including social determinants of health, and the like. In some instances, the one or more required consumer attributes may exceed five. In some instances, the required consumer attributes may be 1000, or more. Health data encrypted tokens 114 are automatically created for aggregated de-identified health data from the de-identified healthcare information dataset 104 and provided to the secure hosted environment 106. Typically, the aggregated de-identified health data from a de-identified healthcare information dataset 104 is obtained from one or more of medical claims, medical remittances, pharmacy claims, dental claims, dental remittances, lab orders, lab results, and the like. Generally, the health data encrypted tokens 114 are created using the same tokenization process used to create the encrypted tokens 110 for the PHI corresponding to the one or more individuals.

Also, the data licensee 102 provides a pre-built executable software package 116 to the secure hosted environment 106 that is installed in a secure container 118 in the secure hosted environment 106. For example, the container 118 may comprise a Docker container in Amazon Web Services (AWS). In some instances, the pre-built executable software package 116 is scanned for any malicious code prior to installation in the secure container 118. The pre-built executable software package 116 comprises computer-executable code to learn and train one or more models 120 using the encrypted tokens 110 and the health data encrypted tokens 114. The pre-built executable software package 116 includes business rules to ensure that training of the one or more models 120 does not increase a risk of re-identification of the PHI corresponding to the one or more individuals. For example, a business rule ensuring that training of the one or more models does not increase the risk of re-identification of the PHI corresponding to the one or more individuals comprises the business rule ensuring that training of the one or more models does not happen on very small cohorts. Other business rules include verifying that outputs of the trained model are adherent to guidelines and/or laws regarding re-identification (e.g., adherent to HIPAA tolerances for re-identification).

The customer data 108 and/or the de-identified customer data 112 and/or the pre-built executable software package 116 may be delivered to the secure hosted environment 106 from the data licensee 102 using any secure communications method such as, for example, sftp, s3 transfer, and the like.

The trained model 120 utilizes the de-identified customer data 112 including the one or more required consumer attributes to create outputs. The outputs from the one or more models 120 are reviewed 122 for data privacy compliance. For example, the data privacy review 122 may be a review of the outputs for HIPAA compliance. During implementation, the data privacy review 122 may be conducted by a data privacy consultant. The implementation reviews by the data privacy consultant can be used to train software to conduct the data privacy review 122. The data privacy review 122 is performed to certify that the outputs have a risk of re-identification of the PHI corresponding to the one or more individuals that remains at or below one or more thresholds of the risk of re-identification of the PHI corresponding to the one or more individuals. Thresholds are used to mathematically/statistically determine the potential risk of reidentification. Typically, the threshold is established by assessing the number of descriptive attributes used and the size of the population being analyzed. A binary of a model, a statistical scoring model, or an aggregate report from the one or more models 120 is provided to the data licensee 102 if the risk of re-identification of the PHI corresponding to the one or more individuals remains at or below the one or more thresholds as determined and certified by the data privacy review 122. If the risk of re-identification is above the threshold, then the binary of the model, statistical scoring model, or the aggregate report is not provided to the data licensee 102. At this point, if the model 120 has outputs that have unacceptable risks of re-identification of the PHI, the model 120 may be further trained or refined, or it may be discarded. In some instances, all thresholds of the risk of re-identification of the PHI corresponding to the one or more individuals, whether met or unmet, are logged within the secure hosted environment 106 for audit purposes. In some instances, an application programming interface (API) with all necessary controls is installed at an edge of the secure hosted environment 106 that allows the data licensee 102 access to only the API, wherein any inputs to the API are pre-defined and certified by the data privacy review 122.

B. Processes and Methods

FIG. 2 is a flowchart illustrating an example of a process for elastically providing data privacy-compliant healthcare analytics. At 202, customer data is received in a secure hosted environment. The customer data is comprised at least in part of PHI corresponding to one or more individuals. At 204, encrypted tokens are created for the PHI. At 206, de-identified customer data is received in the secure hosted environment. The de-identified customer data includes one or more required customer attributes. At 208, health data encrypted tokens are received in the secure hosted environment. The health data encrypted tokens are created for aggregated de-identified health data from a de-identified healthcare information dataset. At 210, a pre-built executable software package is received in the secure hosted environment and installed in a secure container in the secure hosted environment. The pre-built executable software package comprises computer-executable code to learn and train one or more models using the encrypted tokens and the health data encrypted tokens, and the pre-built executable software package includes business rules to ensure that training of the one or more models does not increase a risk of re-identification of the PHI corresponding to the one or more individuals. At 212, outputs from the one or more trained models are reviewed by a data privacy review. The outputs are certified by the data privacy review to ensure the risk of re-identification of the PHI corresponding to the one or more individuals remains at or below one or more thresholds of the risk of re-identification of the PHI corresponding to the one or more individuals. At 214, a binary of a model, statistical scoring model, or an aggregate report (including, for example, eigenvectors of a covariance matrix and non-binary vector autoregression coefficients) from the one or more models are delivered from the secure hosted environment if the risk of re-identification of the PHI corresponding to the one or more individuals remains at or below the one or more thresholds as determined and certified by the data privacy review.

It is to be appreciated that the above method steps are automated and performed by one or more computing devices, such as those described below.

C. Computing Environment

Figure 3:
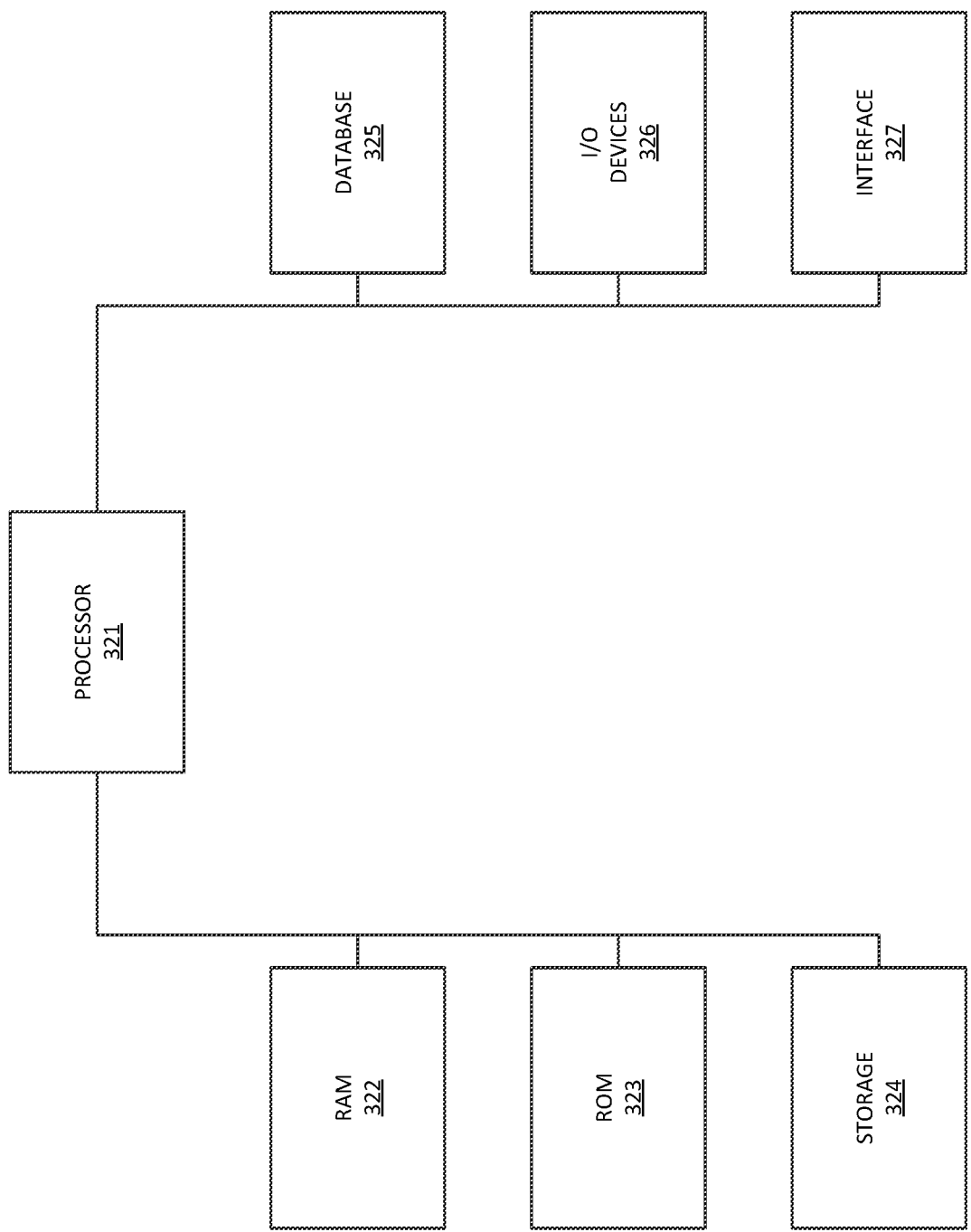
FIG. 3 illustrates an exemplary computer or computing device that can be used for some, a portion of, or all of the set of features and components described herein.

FIG. 3 illustrates an exemplary computer or computing device that can be used for some, a portion of, or all of the features and/or components described herein. All or a portion of the device shown in FIG. 3 may comprise all or any portion of any of the components and devices described herein that may include and/or require a processor or processing capabilities such as used in the secure hosted environment, etc. As used herein, "computer" may include a plurality of computers. The computers may include one or more hardware components such as, for example, a processor 321, a random-access memory (RAM) module 322, a read-only memory (ROM) module 323, a storage 324, a database 325, one or more input/output (I/O) devices 326, and an interface 327. Alternatively, and/or additionally, the computer may include one or more software components such as, for example, a computer-readable medium including computer executable instructions for performing a method or methods associated with the exemplary embodiments. It is contemplated that one or more of the hardware components listed above may be implemented using software. For example, storage 324 may include a software partition associated with one or more other hardware components. It is understood that the components listed above are exemplary only and not intended to be limiting.

Processor 321 may include one or more processors, each configured to execute instructions and process data to perform one or more functions associated with a computer for performing elastic data privacy-compliant healthcare analytics. Processor 321 may be communicatively coupled to RAM 322, ROM 323, storage 324, database 325, I/O devices 326, and interface 327. Processor 321 may be configured to execute sequences of computer program instructions to perform various processes. The computer program instructions may be loaded into RAM 322 for execution by processor 321.

RAM 322 and ROM 323 may each include one or more devices for storing information associated with operation of processor 321. For example, ROM 323 may include a memory device configured to access and store information associated with the computer, including information for identifying, initializing, and monitoring the operation of one or more components and subsystems. RAM 322 may include a memory device for storing data associated with one or more operations of processor 321. For example, ROM 323 may load instructions into RAM 322 for execution by processor 321.

Storage 324 may include any type of mass storage device configured to store information that processor 321 may need to perform processes corresponding with the disclosed embodiments. For example, storage 324 may include one or more magnetic and/or optical disk devices, such as hard drives, CD-ROMs, DVD-ROMs, or any other type of mass media device.

Database 325 may include one or more software and/or hardware components that cooperate to store, organize, sort, filter, and/or arrange data used by the computer and/or processor 321. For example, database 325 may store information and instructions related to the de-identified healthcare information dataset. It is contemplated that database 325 may store additional and/or different information than that listed above.

I/O devices 326 may include one or more components configured to communicate information with a user associated with computer. For example, I/O devices may include a console with an integrated keyboard and mouse to allow a user to maintain the dataset of de-identified healthcare information, and the like. I/O devices 326 may also include a display including a graphical user interface (GUI) for outputting information on a monitor. I/O devices 326 may also include peripheral devices such as, for example, a printer for printing information associated with the computer, a user-accessible disk drive (e.g., a USB port, a floppy, CD-ROM, or DVD-ROM drive, etc.) to allow a user to input data stored on a portable media device, a microphone, a speaker system, or any other suitable type of interface device.

Interface 327 may include one or more components configured to transmit and receive data via a communication network, such as the Internet, a local area network, a workstation peer-to-peer network, a direct link network, a wireless network, or any other suitable communication platform. For example, interface 327 may include one or more modulators, demodulators, multiplexers, demultiplexers, network communication devices, wireless devices, antennas, modems, and any other type of device configured to enable data communication via a communication network.

The computer or computing device illustrated in FIG. 3 may comprise all or a part of a cloud computing environment.

While the methods and systems have been described in connection with preferred embodiments and specific examples, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

Throughout this application, various publications may be referenced. The disclosures of these publications in their entireties are hereby incorporated by reference into this application in order to more fully describe the state of the art to which the methods and systems pertain.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed is:

1. A method of providing data privacy-compliant healthcare analytics comprising:
    receiving, in a secure hosted environment, customer data, wherein at least a portion of the customer data comprises PHI, itself comprising personally identifiable information and/or protected health information corresponding to one or more individuals;
    create encrypted tokens for the PHI corresponding to the one or more individuals;
    receive, in the secure hosted environment, de-identified customer data, wherein the de-identified customer data includes one or more required consumer attributes;
    create health data encrypted tokens for aggregated de-identified health data from a de-identified healthcare information dataset;
    receive, in the secure hosted environment, the health data encrypted tokens for the aggregated de-identified health data;
    receive, in the secure hosted environment, a pre-built executable software package that is installed in a secure container in the secure hosted environment, wherein the pre-built executable software package comprises computer-executable code to learn and train one or more models using the encrypted tokens and the health data encrypted tokens, and wherein the pre-built executable software package includes business rules to ensure that training of the one or more models does not increase a risk of re-identification of the PHI corresponding to the one or more individuals;
    reviewing outputs from the one or more models of the pre-built executable software package by a data privacy review and certifying the outputs to ensure the risk of re-identification of the PHI corresponding to the one or more individuals remains at or below one or more thresholds of the risk of re-identification of the PHI corresponding to the one or more individuals; and
    delivering from the secure hosted environment, a binary of a model, statistical scoring model, or an aggregate report from the one or more models if the risk of re-identification of the PHI corresponding to the one or more individuals remains at or below the one or more thresholds as determined and certified by the data privacy review.

2. The method of claim 1, wherein the secure hosted environment comprises a cloud infrastructure.

3. The method of claim 2, wherein the secure hosted environment is behind a firewall.

4. The method of claim 1, wherein the customer data and/or the de-identified customer data is delivered to the secure hosted environment using any secure communications method.

5. The method of claim 4, wherein the secure communication method comprises one of sftp or s3 transfer.

6. The method of claim 1, wherein the health data encrypted tokens are created using the same tokenization process used to create the encrypted tokens for the PHI corresponding to the one or more individuals.

7. The method of claim 1, wherein the secure container in the secure hosted environment comprises a container in a web service.

8. The method of claim 1, further comprising scanning the pre-built executable software for any malicious code prior to installation in the secure container.

9. The method of claim 1, wherein all thresholds of the risk of re-identification of the PHI corresponding to the one or more individuals, whether met or unmet, are logged within the secure hosted environment for audit purposes.

10. The method of claim 1, wherein the binary of a model or an aggregate report from the one or more models are delivered to a data licensee if the risk of re-identification of the PHI corresponding to the one or more individuals remains at or below the one or more thresholds as determined and certified by the data privacy review.

11. The method of claim 10, further comprising installing at an edge of the secure hosted environment, an application programming interface (API) with all necessary controls that allows the data licensee access to only the API, wherein any inputs to the API are pre-defined and certified by the data privacy review.

12. The method of claim 10, wherein the customer data comprises a use case provided by the data licensee.

13. The method of claim 12, wherein the use case comprises one or more of audience development, program measurement, multi-channel attribution, campaign optimization, "same store" analysis, identify and act on emerging trends, machine Learning and artificial intelligence (AI) algorithms, HCP practice behavior/brand loyalty, planning and strategy, analytics and predictive modeling, referral leakage, and benchmarking and competitive analysis.

14. The method of claim 1, wherein the data privacy review comprises a review for HIPAA compliance.

15. The method of claim 1, wherein one of the business rules ensuring that training of the one or more models does not increase the risk of re-identification of the PHI corresponding to the one or more individuals comprises the business rule ensuring that training of the one or more models does not happen on very small cohorts.

16. The method of claim 1, wherein the aggregated de-identified health data from a de-identified healthcare information dataset is obtained from one or more of medical claims, medical remittances, pharmacy claims, dental claims, dental remittances, lab orders, and lab results.

17. The method of claim 1, wherein the one or more required consumer attributes comprise more than five required consumer attributes.

18. A system for providing data privacy-compliant healthcare analytics, comprising:
    a secure hosted environment;
    a computer that interfaces with the secure hosted environment, wherein the computer comprises at least a processor and a memory, wherein the memory is in communication with the processor, and wherein computer-executable instructions are stored on the memory and executed by the processor, said computer-executable instructions causing the processor to:
    receive, in the secure hosted environment, customer data, wherein at least a portion of the customer data comprises PHI, itself comprising personally identifiable information and/or protected health information corresponding to one or more individuals;
    create encrypted tokens for the PHI corresponding to the one or more individuals;
    receive, in the secure hosted environment, de-identified customer data, wherein the de-identified customer data includes one or more required consumer attributes;
    create health data encrypted tokens for aggregated de-identified health data from a de-identified healthcare information dataset;
    receive, in the secure hosted environment, the health data encrypted tokens for the aggregated de-identified health data;
    receive, in the secure hosted environment, a pre-built executable software package that is installed in a secure container in the secure hosted environment, wherein the pre-built executable software package comprises computer-executable code to learn and train one or more models using the encrypted tokens and the health data encrypted tokens, and wherein the pre-built executable software package includes business rules to ensure that training of the one or more models does not increase a risk of re-identification of the PHI corresponding to the one or more individuals;
    transmit outputs from the one or more models of the pre-built executable software package for review and certification by a data privacy review to ensure the risk of re-identification of the PHI corresponding to the one or more individuals remains at or below one or more thresholds of the risk of re-identification of the PHI corresponding to the one or more individuals; and
    delivering from the secure hosted environment, a binary of a model, statistical scoring model, or an aggregate report from the one or more models if the risk of re-identification of the PHI corresponding to the one or more individuals remains at or below the one or more thresholds as determined and certified by the data privacy review.

19. The system of claim 18, wherein the secure hosted environment comprises a cloud infrastructure behind a firewall.

20. A non-transitory computer program product comprised of computer-executable code stored on a computer-readable medium, said computer-executable code for performing a method comprising:
    receiving, in a secure hosted environment, customer data, wherein at least a portion of the customer data comprises PHI, itself comprising personally identifiable information and/or protected health information corresponding to one or more individuals;
    creating encrypted tokens for the PHI corresponding to the one or more individuals;
    receiving, in the secure hosted environment, de-identified customer data, wherein the de-identified customer data includes one or more required consumer attributes;
    creating health data encrypted tokens for aggregated de-identified health data from a de-identified healthcare information dataset;
    receiving, in the secure hosted environment, the health data encrypted tokens for the aggregated de-identified health data;
    receiving, in the secure hosted environment, a pre-built executable software package that is installed in a secure container in the secure hosted environment, wherein the pre-built executable software package comprises computer-executable code to learn and train one or more models using the encrypted tokens and the health data encrypted tokens, and wherein the pre-built executable software package includes business rules to ensure that training of the one or more models does not increase a risk of re-identification of the PHI corresponding to the one or more individuals;
    receiving a review of outputs from the one or more models of the pre-built executable software package from a data privacy review and certifying the outputs to ensure the risk of re-identification of the PHI corresponding to the one or more individuals remains at or below one or more thresholds of the risk of re-identification of the PHI corresponding to the one or more individuals; and delivering from the secure hosted environment, a binary of a model, statistical scoring model, or an aggregate report from the one or more models if the risk of re-identification of the PHI corresponding to the one or more individuals remains at or below the one or more thresholds as determined and certified by the data privacy review.

\* \* \* \* \*